US008888795B2

(12) United States Patent
Chu

(10) Patent No.: US 8,888,795 B2
(45) Date of Patent: Nov. 18, 2014

(54) SUTURE PASSER

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 757 days.

(21) Appl. No.: 12/184,583

(22) Filed: Aug. 1, 2008

(65) Prior Publication Data

US 2009/0069824 A1 Mar. 12, 2009

Related U.S. Application Data

(60) Provisional application No. 60/970,620, filed on Sep. 7, 2007.

(51) Int. Cl.
*A61B 17/06* (2006.01)
*A61B 17/04* (2006.01)
*A61B 17/221* (2006.01)
*A61B 17/42* (2006.01)
*A61B 17/00* (2006.01)

(52) U.S. Cl.
CPC ..... *A61B 17/0485* (2013.01); *A61B 2017/2212* (2013.01); *A61B 2017/4216* (2013.01); *A61B 2017/00805* (2013.01); *A61B 2017/06052* (2013.01)
USPC ............................ 606/144; 606/148; 606/139

(58) Field of Classification Search
USPC ......... 606/192, 205, 113, 139–148, 213, 222, 606/228; 604/177, 170.01; 623/1.11
See application file for complete search history.

(56) References Cited

U.S. PATENT DOCUMENTS

| 4,441,497 | A |   | 4/1984 | Paudler |
| 5,281,237 | A | * | 1/1994 | Gimpelson ............ 606/144 |
| 5,312,351 | A | * | 5/1994 | Gerrone ............... 604/117 |
| 5,342,369 | A |   | 8/1994 | Harryman, II |
| 5,350,385 | A | * | 9/1994 | Christy ................ 606/139 |
| 5,387,227 | A | * | 2/1995 | Grice .................. 606/222 |
| 5,403,331 | A |   | 4/1995 | Chesterfield et al. |
| 5,439,467 | A |   | 8/1995 | Benderev et al. |
| 5,447,512 | A | * | 9/1995 | Wilson et al. ........... 606/139 |

(Continued)

FOREIGN PATENT DOCUMENTS

EP  1 477 121 A2  11/2004
WO  WO 92/05828 A1  4/1992

(Continued)

OTHER PUBLICATIONS

International Search Report and Written Opinion for PCT/US08/73454, mailed on Jan. 29, 2009; 11 pages.

(Continued)

*Primary Examiner* — Mark Mashack

(57) ABSTRACT

An apparatus includes an elongate member, an actuator, and a thread member. A portion of the elongate member defines a central axis. The elongate member defines a slot which extends along an axis parallel to the central axis. The actuator is coupled to the elongate member and is accessible through the slot. The actuator is moveable from a first position to a second position different than the first position. The thread member is coupled to the actuator and has a receiving portion. The thread member is moveable from a first position to a second position different than the first position when the actuator is moved from its first position to its second position.

18 Claims, 10 Drawing Sheets

(56) References Cited

U.S. PATENT DOCUMENTS

| | | |
|---|---|---|
| 5,462,562 A | 10/1995 | Elkus |
| 5,501,692 A | 3/1996 | Riza |
| 5,562,683 A | 10/1996 | Chan |
| 5,562,684 A | 10/1996 | Kammerer |
| 5,562,687 A | 10/1996 | Chan |
| 5,643,292 A * | 7/1997 | Hart .............................. 606/144 |
| 5,658,299 A * | 8/1997 | Hart .............................. 606/139 |
| 5,681,333 A | 10/1997 | Burkhart et al. |
| 5,697,950 A | 12/1997 | Fucci et al. |
| 5,746,752 A | 5/1998 | Burkhart |
| 5,746,754 A | 5/1998 | Chan |
| 5,752,968 A * | 5/1998 | Jolly et al. .................... 606/167 |
| 5,755,728 A | 5/1998 | Maki |
| 5,776,151 A | 7/1998 | Chan |
| 5,800,447 A | 9/1998 | Wenstrom, Jr. |
| 5,816,258 A | 10/1998 | Jervis |
| 5,817,111 A * | 10/1998 | Riza .............................. 606/148 |
| 5,906,624 A | 5/1999 | Wenstrom, Jr. |
| 5,910,148 A | 6/1999 | Reimels et al. |
| 6,022,360 A * | 2/2000 | Reimels et al. ............... 606/144 |
| 6,045,574 A | 4/2000 | Thal |
| 6,048,351 A | 4/2000 | Gordon et al. |
| 6,059,789 A | 5/2000 | Dinger et al. |
| 6,368,335 B1 | 4/2002 | Chan |
| 6,547,807 B2 | 4/2003 | Chan et al. |
| 6,629,984 B1 | 10/2003 | Chan |
| 6,638,283 B2 | 10/2003 | Thal |
| 6,719,765 B2 | 4/2004 | Bonutti |
| 6,932,826 B2 | 8/2005 | Chan |
| 6,991,636 B2 | 1/2006 | Rose |
| 7,041,111 B2 | 5/2006 | Chu |
| 7,108,700 B2 | 9/2006 | Chan |
| 2001/0016747 A1 | 8/2001 | Romano et al. |
| 2002/0077532 A1* | 6/2002 | Gannoe et al. ................. 600/232 |
| 2003/0023250 A1 | 1/2003 | Watschke et al. |
| 2004/0087970 A1 | 5/2004 | Chu et al. |
| 2005/0033324 A1* | 2/2005 | Phan .............................. 606/148 |
| 2005/0085850 A1* | 4/2005 | Harris et al. ................... 606/205 |
| 2005/0165417 A1* | 7/2005 | Sauer et al. .................... 606/144 |
| 2005/0240076 A1* | 10/2005 | Neisz et al. ...................... 600/30 |
| 2006/0173468 A1* | 8/2006 | Simmon et al. ............... 606/113 |
| 2007/0179510 A1* | 8/2007 | Stone ............................. 606/148 |

FOREIGN PATENT DOCUMENTS

| | | |
|---|---|---|
| WO | WO 01/93656 A2 | 12/2001 |
| WO | 2006081545 A1 | 8/2006 |
| WO | WO 2006/081545 | 8/2006 |

OTHER PUBLICATIONS

International Preliminary Report on Patentability for PCT Application No. PCT/US2008/073454, mailed on Mar. 18, 2010, 8 pages.

\* cited by examiner

SUTURE PASSER

CROSS-REFERENCE TO RELATED APPLICATIONS

This application claims priority to U.S. Provisional Application Ser. No. 60/970,620, entitled "Suture Passer," filed Sep. 7, 2007, which is incorporated herein by reference in its entirety.

BACKGROUND

The invention relates to passing a suture or other thread-like object within a body, and more particularly to a looped suture passer to assist in passing at least a portion of a suture or other thread-like object through bodily tissue.

In various corrective surgeries or implant procedures, bodily tissue must be returned to a certain anatomical position or placed in an improved position. For example, when uterine prolapse occurs, weakened ligaments cause the uterus to descend into the vaginal cavity. One way to correct uterine prolapse requires that the vaginal apex be approximated to the sacrospinous ligament. The uterus is suspended by sutures that are passed through the vaginal wall. Passing sutures through the vaginal wall, however, is difficult as there is limited space to work in.

Because passing a suture is often difficult due to the limited space available to work in, devices and techniques have been developed to assist a person, such as a surgeon, in manipulating sutures. Some sutures are manipulated by plunger-type suture passing devices, whereby a surgeon squeezes a handle to move a plunger which projects a loop through a guide tip. The handle of such plunger-type devices must be squeezed to slide the plunger so that the loop is extended, thus requiring at least two fingers to operate the devices. In some case, the plunger-type devices also have obtrusive handles, which can impair maneuverability of the device when working in confined spaces. For example, during surgery, a surgeon may utilize multiple devices all directed toward use in a small portion of the patient's body. As such, the confined surgical work space can become cluttered with devices and thus impair maneuverability of individual devices. Therefore, a compact device would grant the surgeon greater ease of maneuverability in the confined surgical work space.

There is, therefore, a need for an improved suture passing device in which a surgeon can move the actuator of the device with a single finger or thumb. This allows the surgeon to more easily and steadily control the operation of the suture passing device, and thus the manipulation of the suture. There is also a need for an improved suture passing device that has a compact handle portion thus allowing for greater maneuverability of a device within a confined surgical work space.

SUMMARY OF THE INVENTION

An apparatus includes an elongate member, an actuator, and a thread member. A portion of the elongate member defines a central axis. The elongate member defines a slot which extends along an axis parallel to the central axis. The actuator is coupled to the elongate member and is accessible through the slot. The actuator is moveable from a first position to a second position different than the first position. The thread member is coupled to the actuator and has a receiving portion. The thread member is moveable from a first position to a second position different than the first position when the actuator is moved from its first position to its second position. A portion of the thread member is disposed within a lumen defined by the elongate member when the thread member is in its first position. At least a portion of the thread member extends from a distal opening defined by the elongate member when the thread member is in its second position.

DETAILED DESCRIPTION OF THE INVENTION

Figure 1:
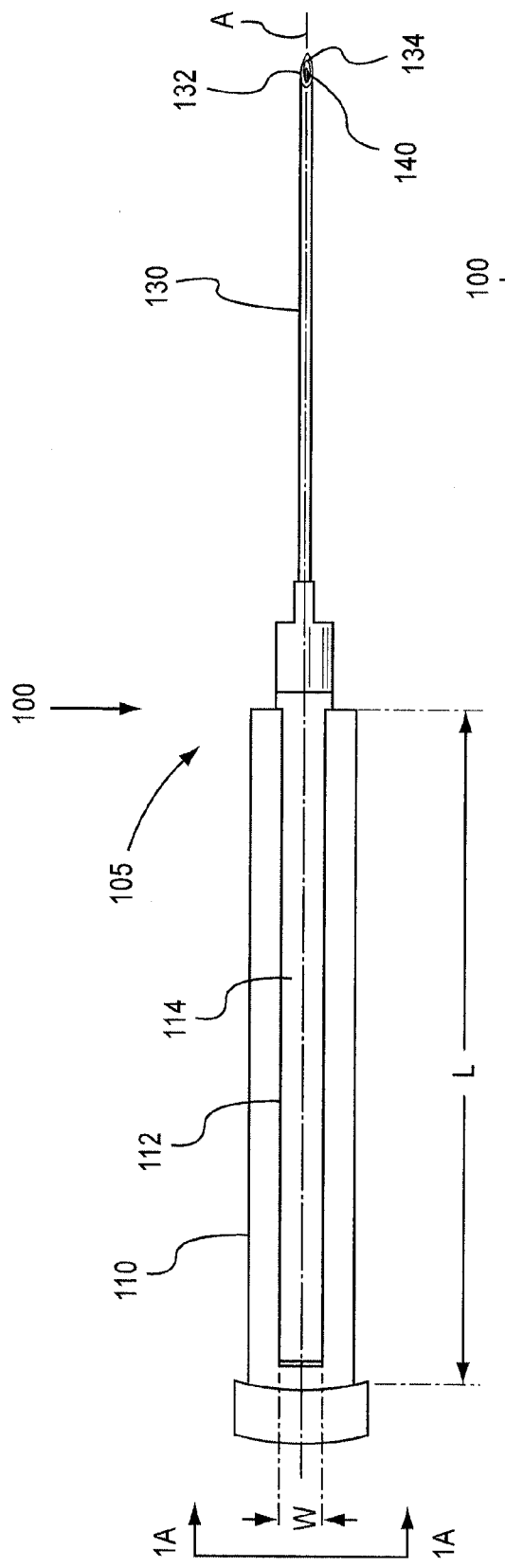
FIGS. 1-1A are side and end views, respectively, of an apparatus according to an embodiment of the invention.
Figure 1A:
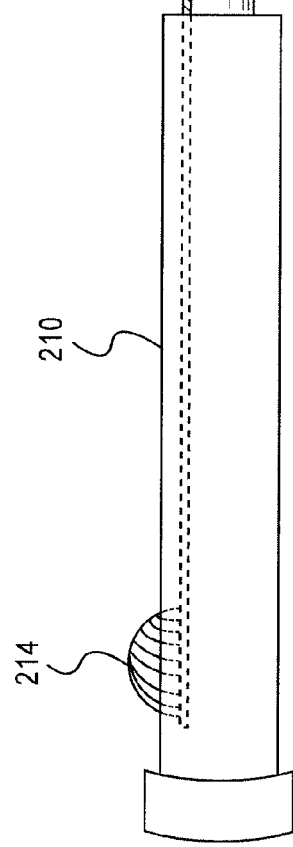

As illustrated in FIG. 1, an apparatus 100 according to an embodiment of the invention includes an elongate member 105, an actuator 114, and a thread member 140. The elongate member 105 has a handle portion 110 and a shaft portion 130. The elongate member 105 extends along and defines a central axis A. The shaft portion 130 defines a lumen 132 along central axis A and has a distal opening 134. A portion of a thread member 140 is disposed within the lumen 132 of the shaft portion 130. As illustrated in FIGS. 1 and 1A, the apparatus 100 is compactly configured. Specifically, the elongate member 105 is substantially cylindrical and has no large protrusions perpendicular to axis A when the apparatus 100 is viewed from an end view.

The handle portion 110 of the elongate member 105 defines a slot 112. As illustrated in FIG. 1, the slot 112 can be an elongate slot having a length L that is greater than the width W of the slot. The elongate slot 112 extends parallel to the central axis A of a portion of the elongate member 105. In other words, the length L of the slot 112 extends parallel to the central axis A.

The actuator 114 is coupled to the handle portion 110. For example, in the embodiment illustrated in FIG. 1, the actuator 114 is slidably coupled to the handle portion 110 and is accessible through the elongate slot 112. In the illustrated embodiment, the actuator 114 is located within the elongate slot 112 and below the surface of the handle portion 110. An operator can access the actuator 114 by placing his thumb or other finger over the elongate slot 112 and applying enough pressure so that the pad or tip of his thumb or finger enters the elongate slot to contact the actuator.

Figure 3:
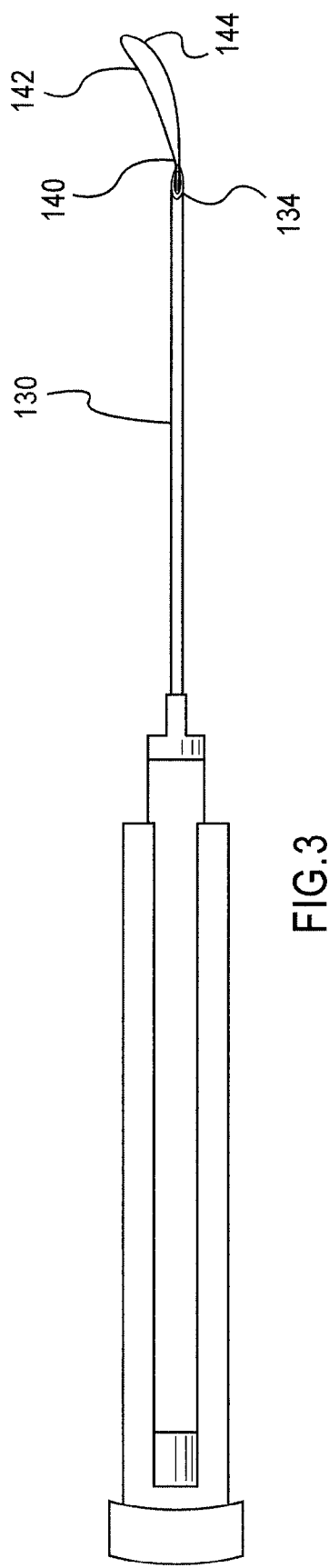
FIGS. 3-4 are side views of the apparatus of FIG. 1 with a thread member extended from the distal end portion of the apparatus.
Figure 4:
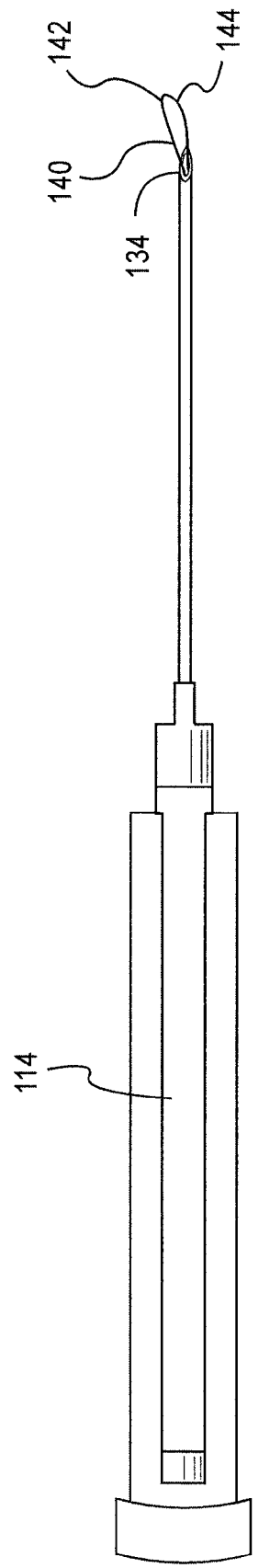

The actuator 114 can be configured to move to or between two or more positions along a continuum parallel to central axis A; the continuum extending between a position in which the actuator is fully retracted into the handle portion 110 and a position in which the actuator is fully extended from the handle portion. Specifically, in the illustrated embodiment, the actuator 114 can move from a first position (FIG. 1), to a second position different than the first position (FIG. 3), and to a third position that is different than the first position and the second position (FIG. 4).

The actuator 114 remains in one position until it is moved to a different position. For example, the actuator 114 remains in the first position until an operator moves the actuator to the second or third position. The actuator 114 can remain (or be retained) in a position by any known means for retention. For example, in some embodiments, the actuator can remain in position by means of interlocking teeth. In that manner, teeth on the actuator can lock into grooves formed by complementary teeth inside the handle portion and beneath the actuator. An operator must apply pressure to the actuator to release the teeth from the grooves and move the actuator. In another example, in some embodiments, the actuator remains in position by means of a resistance fit. In that manner, the actuator fits tightly within the handle portion such that an operator must apply pressure to move the actuator to another position.

The thread member 140 is coupled to the actuator 114. For example, a proximal end portion (not shown) can be coupled to the actuator 114. In that manner, the thread member 140 moves corresponding to movement of the actuator 114. For example, the thread member 140 moves from a first position (FIG. 1) to a second position different than the first position (FIG. 3) or to a third position different than the first and second positions (FIG. 4) when the actuator 114 is moved from its first position to its second or third position, respectively. In an embodiment in which the actuator 114 moves to a position different than its first, second, or third position, the thread member 140 correspondingly moves to a position different than its first, second, and third positions.

Figure 5:
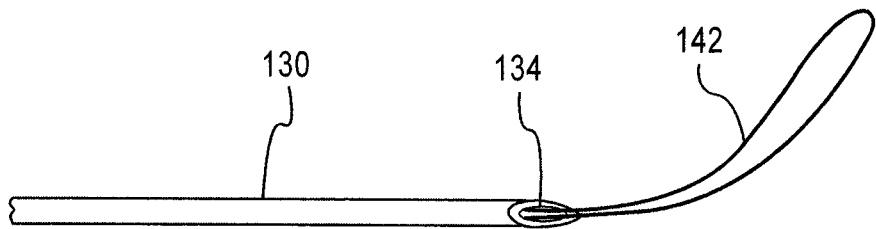
FIGS. 5-9 are side views of distal end portions of apparatuses according to embodiments of the invention.

The thread member 140 includes a receiving portion 142. The receiving portion 142 is configured to receive a thread-like object, such as a suture, during a surgical procedure. In the embodiment illustrated in FIGS. 3 and 4, the receiving portion 142 is implemented as a loop 144. As illustrated in FIG. 5, in one embodiment, the receiving portion 142 includes a curved section or portion when at least a portion of the receiving portion extends from the distal opening 134 of the shaft portion 130.

In the embodiment illustrated in FIG. 1, at least a portion of the thread member 140 is disposed within the lumen 132 of the shaft portion 130 when the thread member is in its first position. In one embodiment, the entire thread member 140 is disposed within the lumen 132 of the shaft portion 130 when the thread member is in its first position. As illustrated in FIG. 3, when the thread member 140 is in its second position, at least a portion of the receiving portion 142 of the thread member extends from the distal opening 134 of the shaft portion 130. When the thread member 140 is in a position different than its first or second position, the receiving portion 142 moves correspondingly, either extending from the distal opening 134 of the shaft portion 130 or retracting into the lumen 132 of the shaft portion. For example, by placing the thread member 140 in a third position, as illustrated in FIG. 4, the receiving portion 142 can be partially extended from the lumen 132. In another example, the thread member 140 can move to a position such that the receiving portion 142 is disposed entirely within the lumen 132 of the shaft portion 130. In other words, the degree of extension of the receiving portion 142 from the shaft portion 130 depends upon the position of the thread member 140, which depends upon the position of the actuator 114.

In some embodiments, the thread member 140 is formed of flexible material. In some embodiments, the thread member 140 is configured to have a predetermined shape when the portion of the thread member extends from the distal opening of the lumen 132. For example, in one embodiment, the receiving portion 142 is formed of a shape memory material, such as nitinol. In that manner, the receiving portion 142 has a predetermined shape when the receiving portion is extended from the lumen 132 of the shaft portion 130 after being at least partially straightened and compressed while retracted within the lumen. For example, the receiving portion 142 may have a curved shape, an S-shape, or other shape, when the receiving portion extends from the lumen 132. In one embodiment, the receiving portion is made of nitinol, a nickel and titanium alloy with shape memory capabilities. A receiving portion made of shape memory material, such as nitinol, is able to be preconfigured into a desired shape, retracted into and thus at least partially straightened within the lumen 132, and then return to its preconfigured shape when the receiving portion is extended from the lumen.

Figure 10:
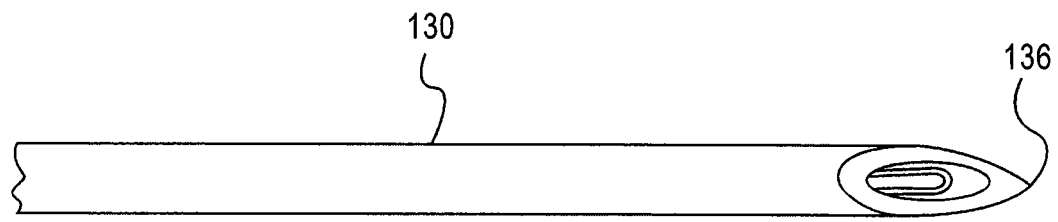
FIG. 10 is a side view of a distal end portion of the apparatus of FIG. 1.
Figure 11:
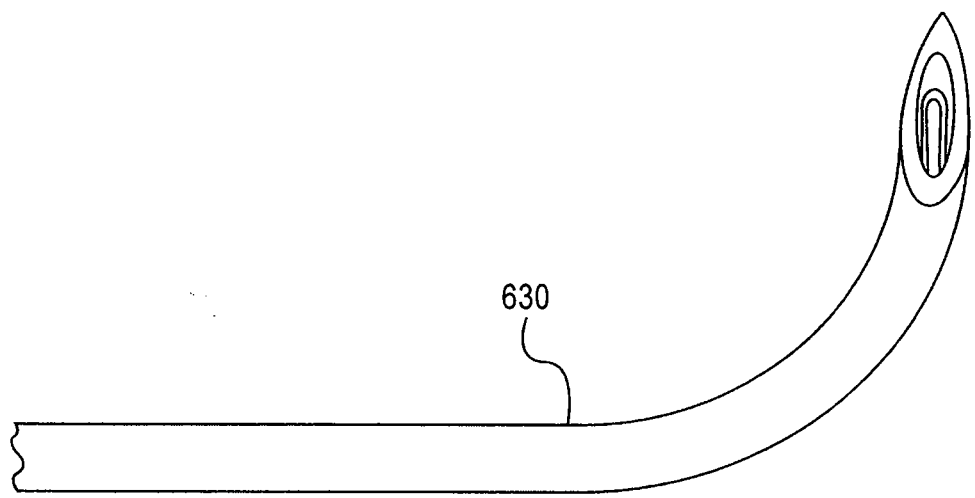
FIG. 11 is a side view of a distal end portion of an apparatus according to an embodiment of the invention.

One embodiment of the invention, best illustrated in FIG. 10, includes a straight shaft portion 130 that is formed as a straight cylindrical tube with an angled, sharp distal tip 136 (similar to a hypodermic needle). In other embodiments, the shaft portion 630 is curved at a predetermined angle, as illustrated in FIG. 11. For example, the shaft portion 630 can be a cylindrical tube curved into an L- or J-shape, or a semi-circle. In other embodiments, the shaft portion 130 has a blunt distal tip (not shown).

A system for passing a suture through bodily tissue includes an apparatus, such as apparatus 100 previously described, and a backstop 150. The backstop 150 includes a first end portion 153 and a second end portion 157. The first end portion 153 of the backstop 150 is a grip portion. The grip portion is for placing the backstop 150 in a desired location and for holding the backstop in place. At least a portion of the backstop 150 is configured to be inserted into a body cavity. The second end portion 157 is configured to stop the distal tip 136 of the shaft portion 130 of the apparatus 100, such that the second end portion of the backstop 150 prevents the distal tip of the shaft portion of the apparatus from inadvertently puncturing bodily tissue. In other words, when the backstop 150 is between a first bodily tissue and a second bodily tissue and the distal tip 136 of the apparatus 100 is inserted through the first bodily tissue, the distal tip of the apparatus comes into contact with the backstop and the backstop stops further insertion of the distal tip and prevents the distal tip from puncturing the second bodily tissue. In one embodiment, the second end portion 157 of the backstop 150 defines a soft distal pad (not shown). In such an embodiment, for example, the soft distal pad can be a foam material that covers the tip of the distal end portion. In another example, the soft distal pad can be made of gauze, rubber, or other material configured to receive or engage the distal tip 136 of the apparatus 100.

Figure 12:
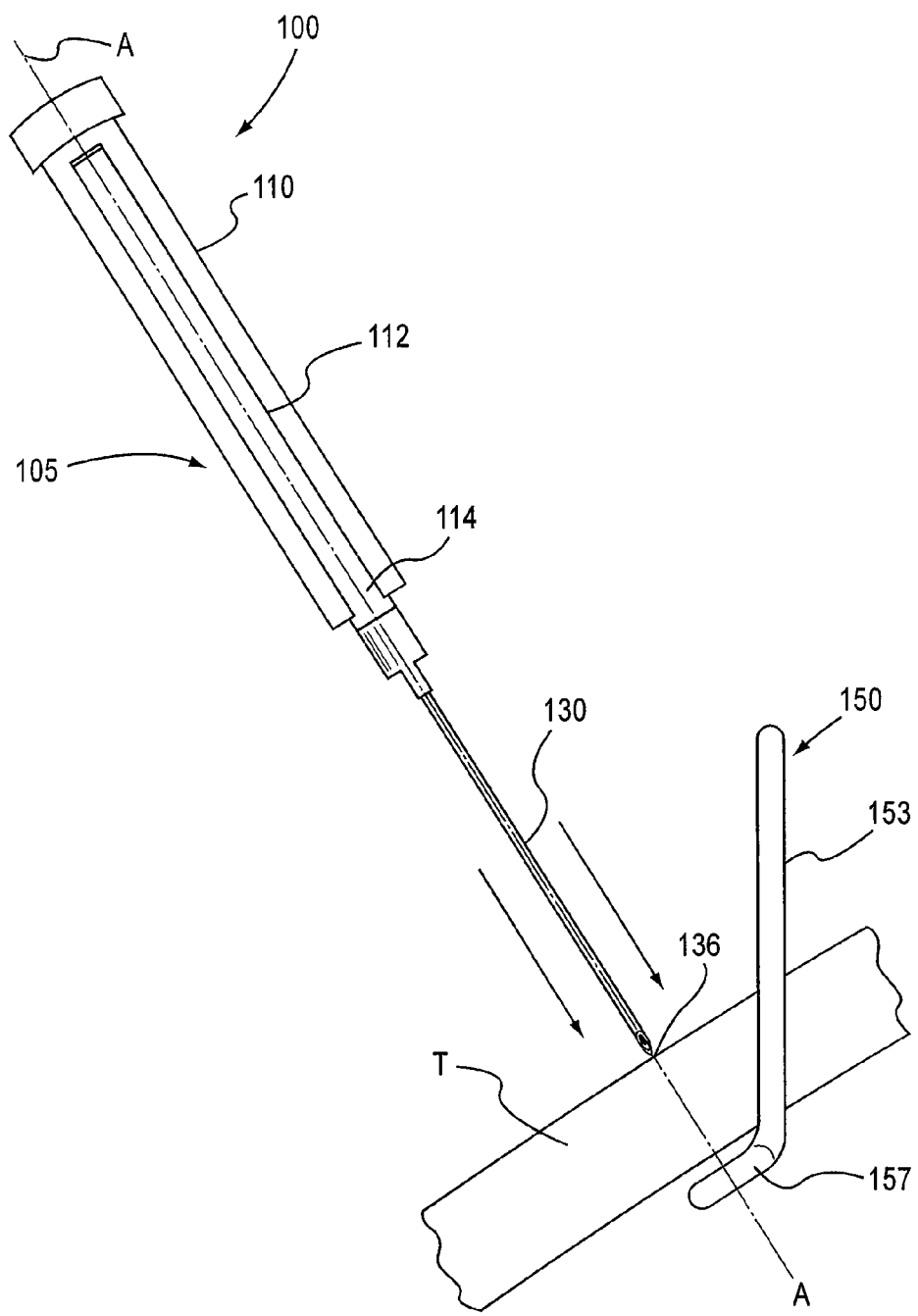
FIG. 12 shows an apparatus according to an embodiment of the invention being inserted into bodily tissue.

As best illustrated in FIGS. 12 through 15, the apparatus 100 may be used to collect or otherwise recover a suture or other thread-like object disposed in a body of a patient. As illustrated in FIG. 12, the shaft portion 130 of the elongate member 105 is inserted into a target tissue T within a body cavity. For example, the shaft portion 130 can penetrate a connective and/or muscle tissue. A backstop 150 is inserted between the tissue T and other bodily tissue prior to inserting the shaft portion 130. In this manner, the backstop 150 helps prevent the shaft portion 130 from puncturing tissue other than the target tissue T as the shaft portion 130 is inserted through tissue T. The backstop 150 can be removed after inserting the shaft portion 130 into tissue T.

Figure 13:
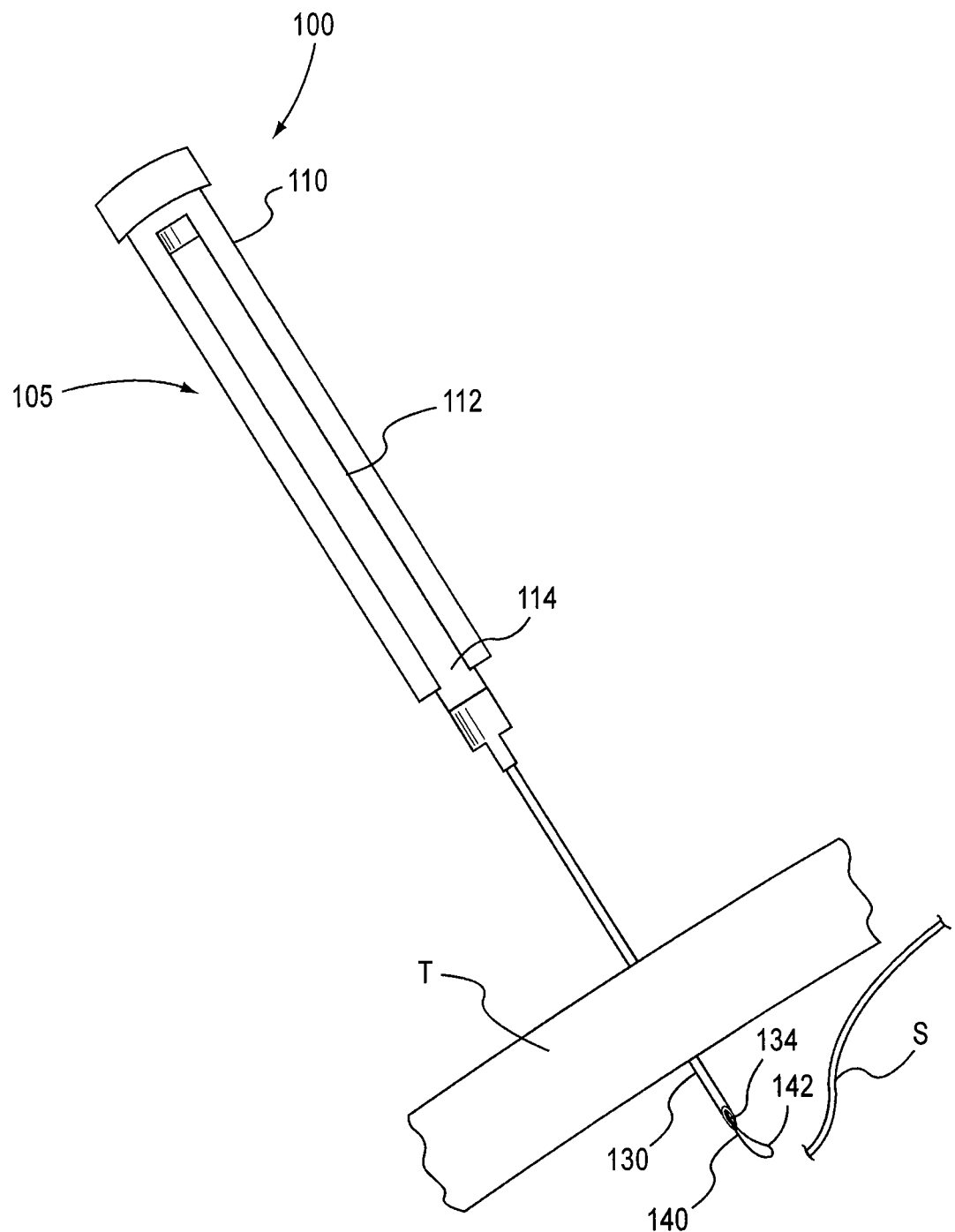
FIG. 13 shows an apparatus according to an embodiment of the invention inserted through bodily tissue.

The actuator 114 is accessed through the elongate slot 112 of the handle portion 110 of the elongate member 105. The actuator 114 is moved along an axis, such as a longitudinal axis, parallel to a central axis A of the elongate slot 112 from its first position to its second position different than the first position. As illustrated in FIG. 13, moving the actuator 114 to the second position causes the receiving portion 142 of the thread member 140 to extend from a distal opening 134 of the shaft portion 130 of the elongate member 105.

Figure 14:
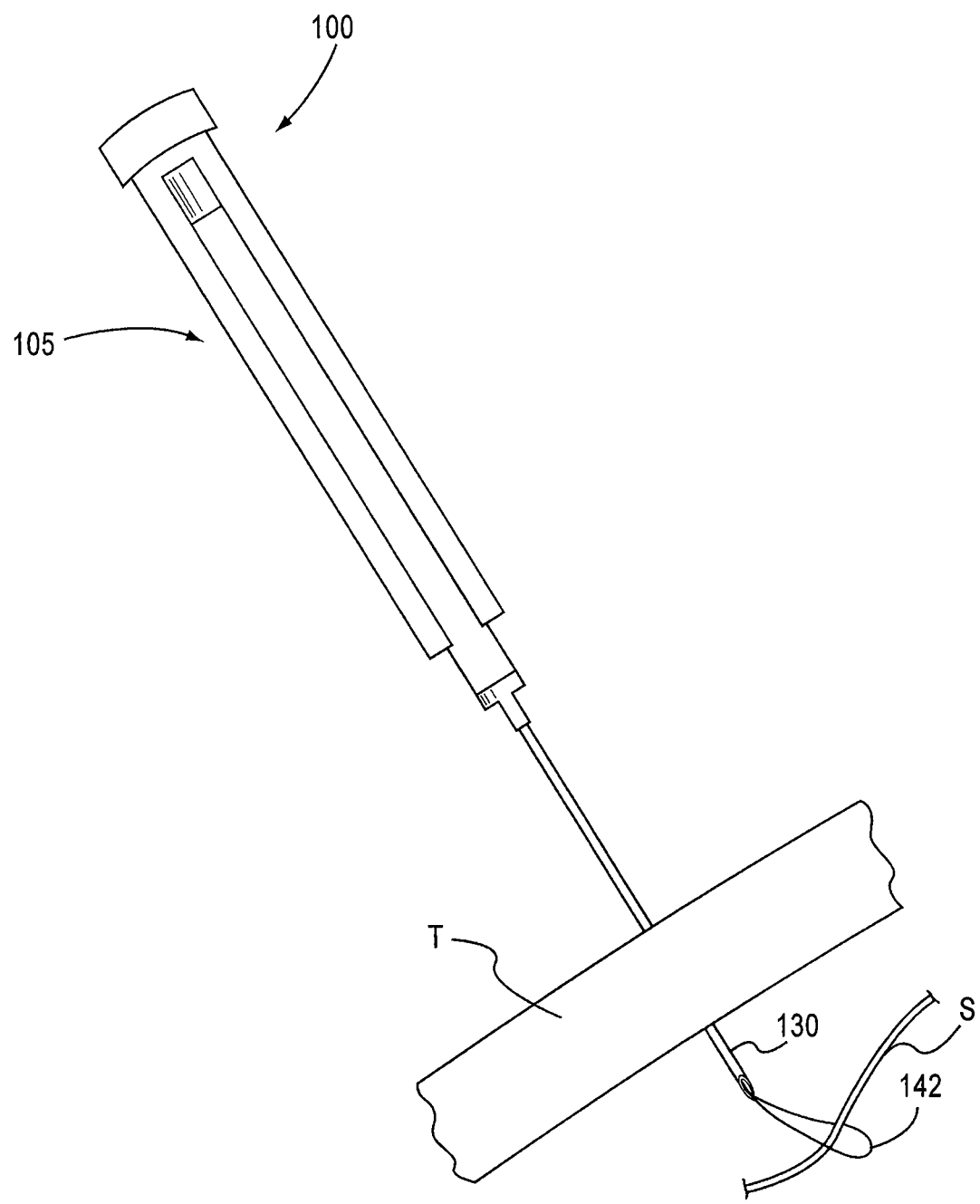
FIG. 14 shows an apparatus according to an embodiment of the invention receiving a suture through a receiving portion.
Figure 15:
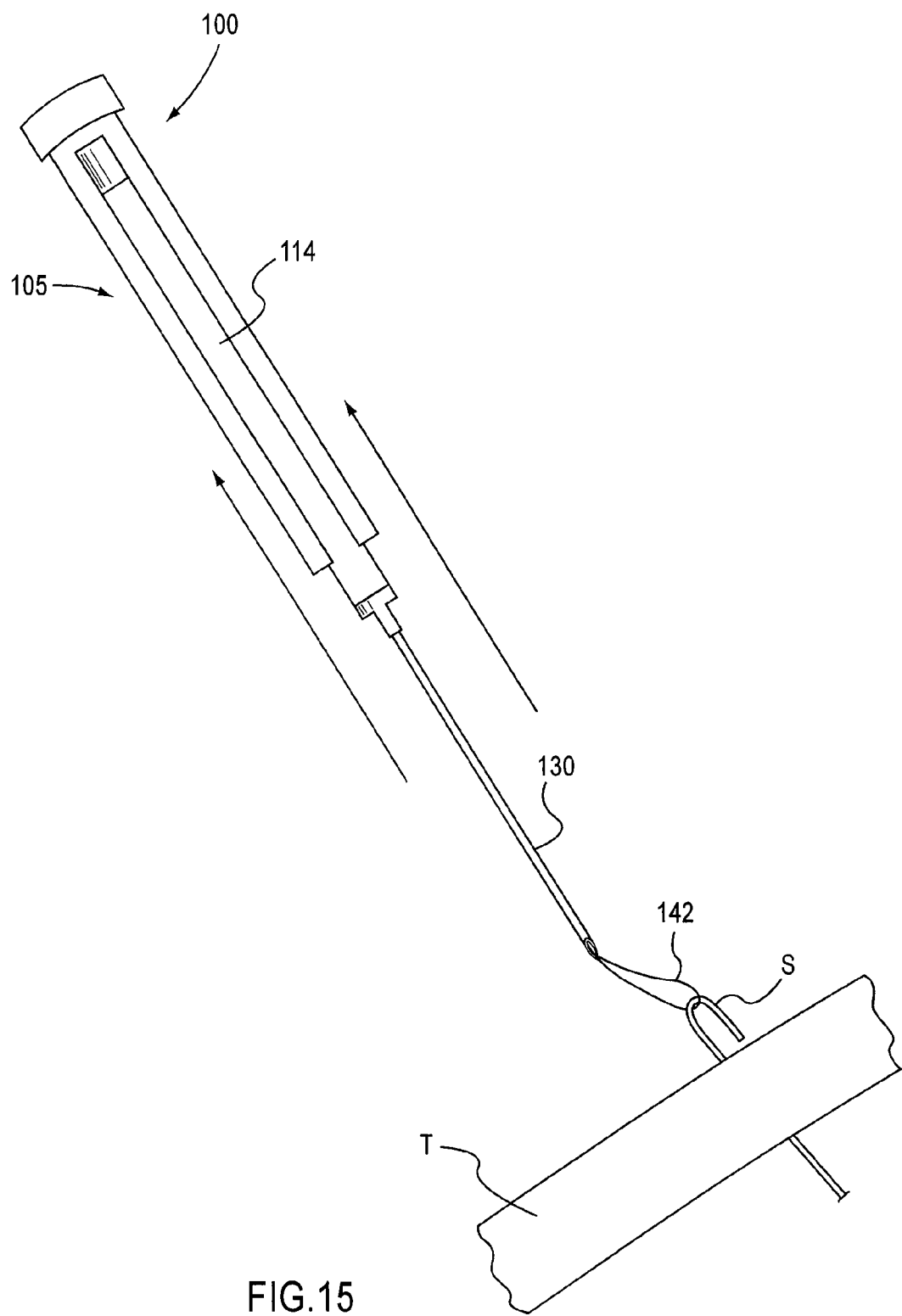
FIG. 15 shows an apparatus according to an embodiment of the invention being withdrawn from bodily tissue and withdrawing a suture through the bodily tissue.

As illustrated in FIG. 14, a suture S is passed through the extended receiving portion 142. As illustrated in FIG. 15, the shaft portion 130 of the elongate member 105 is withdrawn from the tissue T while the receiving portion 142 is extended and the suture S remains passed through the receiving portion 142. In the illustrated embodiment, the actuator 114 remains in its second position and the receiving portion 142 remains in its second position as the shaft portion 130 is withdrawn from the tissue T.

The apparatus 100 may be used, for example, to pass a suture through bodily tissue during a procedure to repair uterine prolapse. One way to repair or correct uterine prolapse includes using sutures to suspend the uterus in an anatomically correct position. In such a procedure, the sutures are passed through an anchor location, such as the sacrospinous ligament. This can be accomplished by using a known suture throwing device or a suture placement device, such as the Capio® CL Transvaginal Suture Capturing Device or the Capio® Standard Suture Capturing Device, both of which are available from Boston Scientific Scimed, Inc. of Maple Grove, Minn. The apparatus 100 can then be inserted through another portion of bodily tissue, such as a vaginal wall. The actuator 114 is actuated to extend the receiving portion 142. The receiving portion 142 of the apparatus 100 is oriented to receive the suture. The suture is received in the receiving portion 142 of the apparatus 100. The apparatus 100 is withdrawn through the bodily tissue to pass the suture through the vaginal wall. During the procedure, a backstop 150 can be inserted between the vaginal wall and another portion of the body, such as the bladder of the patient, to prevent inadvertent puncture of such other portion of the body.

Figure 2:
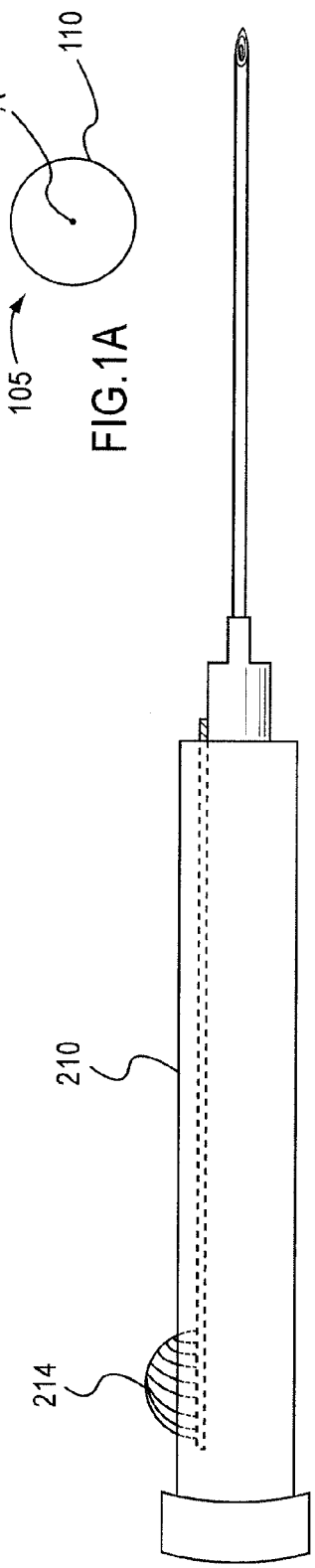
FIG. 2 is a side view of an apparatus according to an embodiment of the invention.

While various embodiments of the invention have been described above, it should be understood that they have been presented by way of example only, and not limitation. For example, although the actuator 114 is illustrated and described above as being below the surface of the handle portion 110, in another embodiment, as illustrated in FIG. 2, a portion of the actuator 214 extends from the elongate slot (not shown), such that it is accessible at or above the surface of the handle portion 210.

Figure 6:
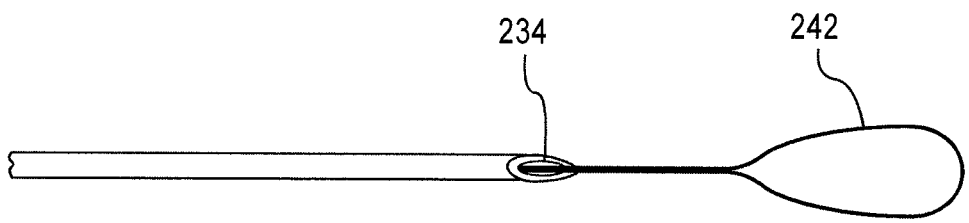
Figure 7:
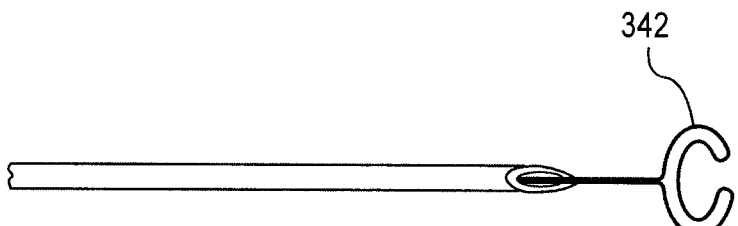
Figure 8:
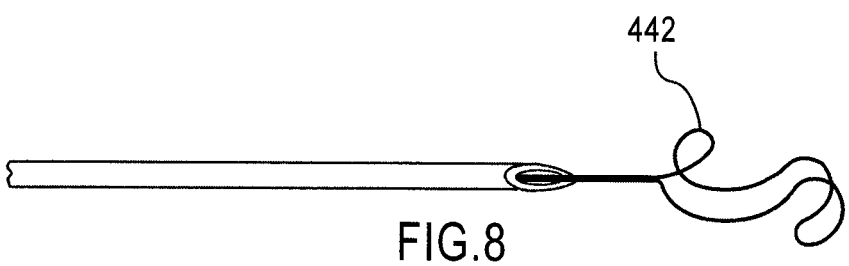
Figure 9:
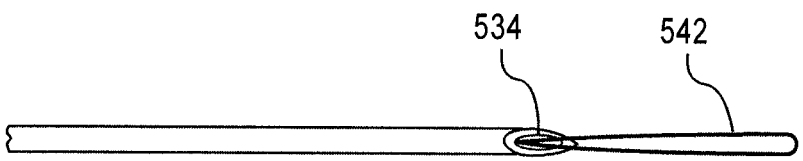

In another example, although the receiving portion 142 is illustrated and described above as being a curved loop, in other embodiments, the receiving portion has another shape. For example, as illustrated in FIG. 6, the receiving portion 242 can be straight or flat when extended from a distal opening 234. In another example, the receiving portion 342 can be C-shaped, as illustrated in FIG. 7. The receiving portion 442 can be S-shaped, as illustrated in FIG. 8. In yet another example, the receiving portion 542 can be U-shaped when extended from the distal opening 534, as illustrated in FIG. 9. It should be understood that although various shaped receiving portions are illustrated, in other embodiments of the invention, the receiving portion of the thread member may be of any shape that can receive a suture or other thread-like object.

Although the thread member 140 is described above as being formed of a flexible material, in other embodiments, at least a portion of the thread member can be formed of a rigid material. For example, the portion of the thread member proximate to the actuator may be made of a rigid material, or a material more rigid than the flexible material of which the receiving portion is made.

In another example, although various shaped shaft portions are illustrated and described above, in other embodiments of the invention, the shaft portion may be of any shape that can be inserted into bodily tissue and that can dispose at least a portion of a thread member within its lumen. Although the shaft portion of the elongate member has been illustrated and described as being curved in some embodiments, in other embodiments, any portion of the elongate member can have a curved shape. In some embodiments, a portion of the elongate member, such as the shaft portion, is bendable or shapeable. In this manner, an operator can configure the portion of the elongate member into a desirable shape to suit the individual need of the patient. For example, the bendable or shapeable portion of the elongate member can be constructed of a bendable or shapeable material, such as a nitinol tubing.

Although the actuator 114 is described above as remaining in a position until moved by an operator to a different position, in other embodiments, the actuator is biased towards a predetermined position. For example, the actuator can be biased towards its first position such that the actuator returns to its first position when the operator stops applying pressure to the actuator.

In yet another example, although the slot 112 has been illustrated and described as being elongate, in other embodiments, the slot can be any suitable shape suitable for allowing movement of the actuator 114 between its first position, second position, and/or third position.

Figure 16:
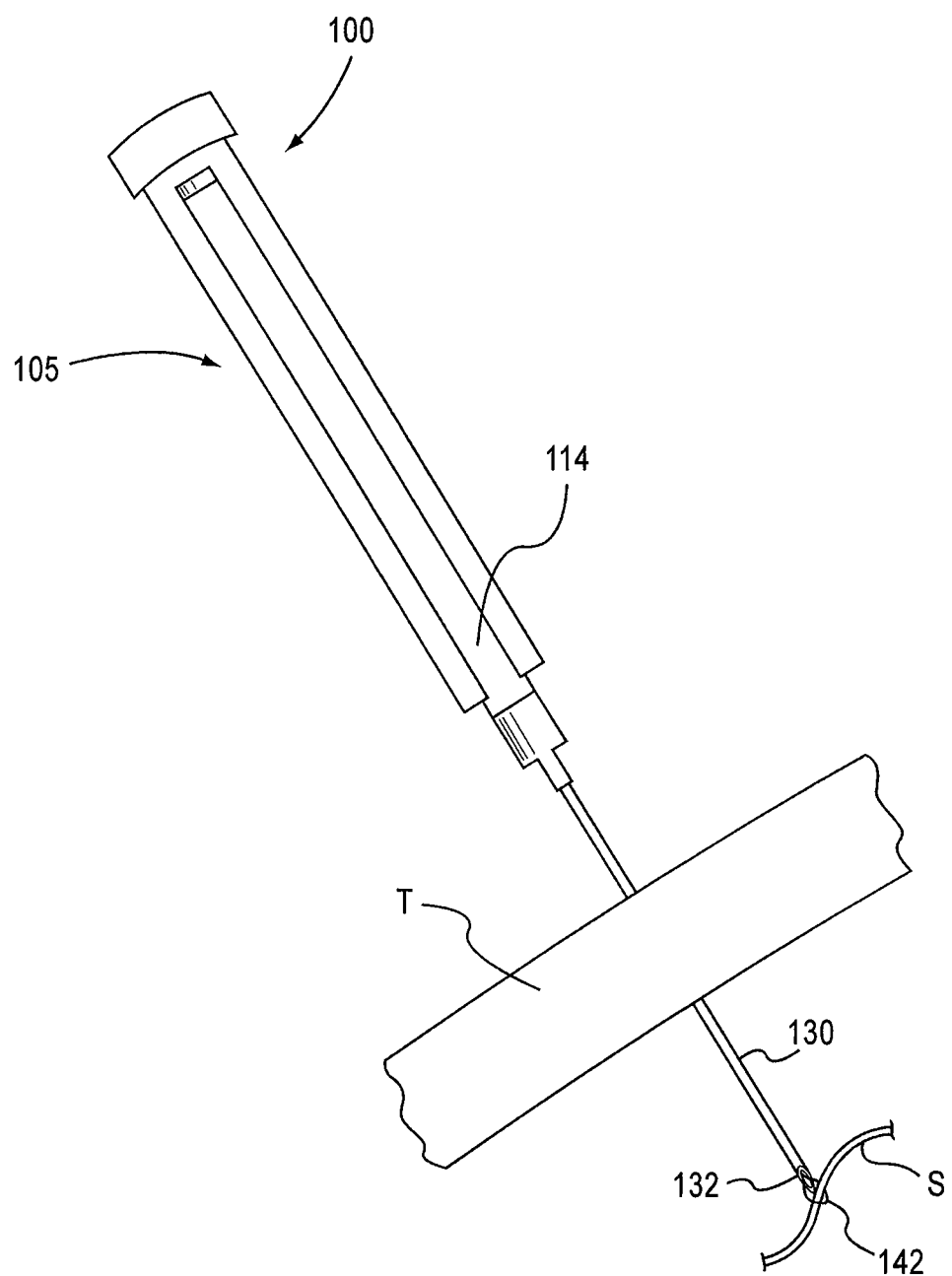
FIG. 16 shows an apparatus according to an embodiment of the invention receiving a suture through a receiving portion.
Figure 17:
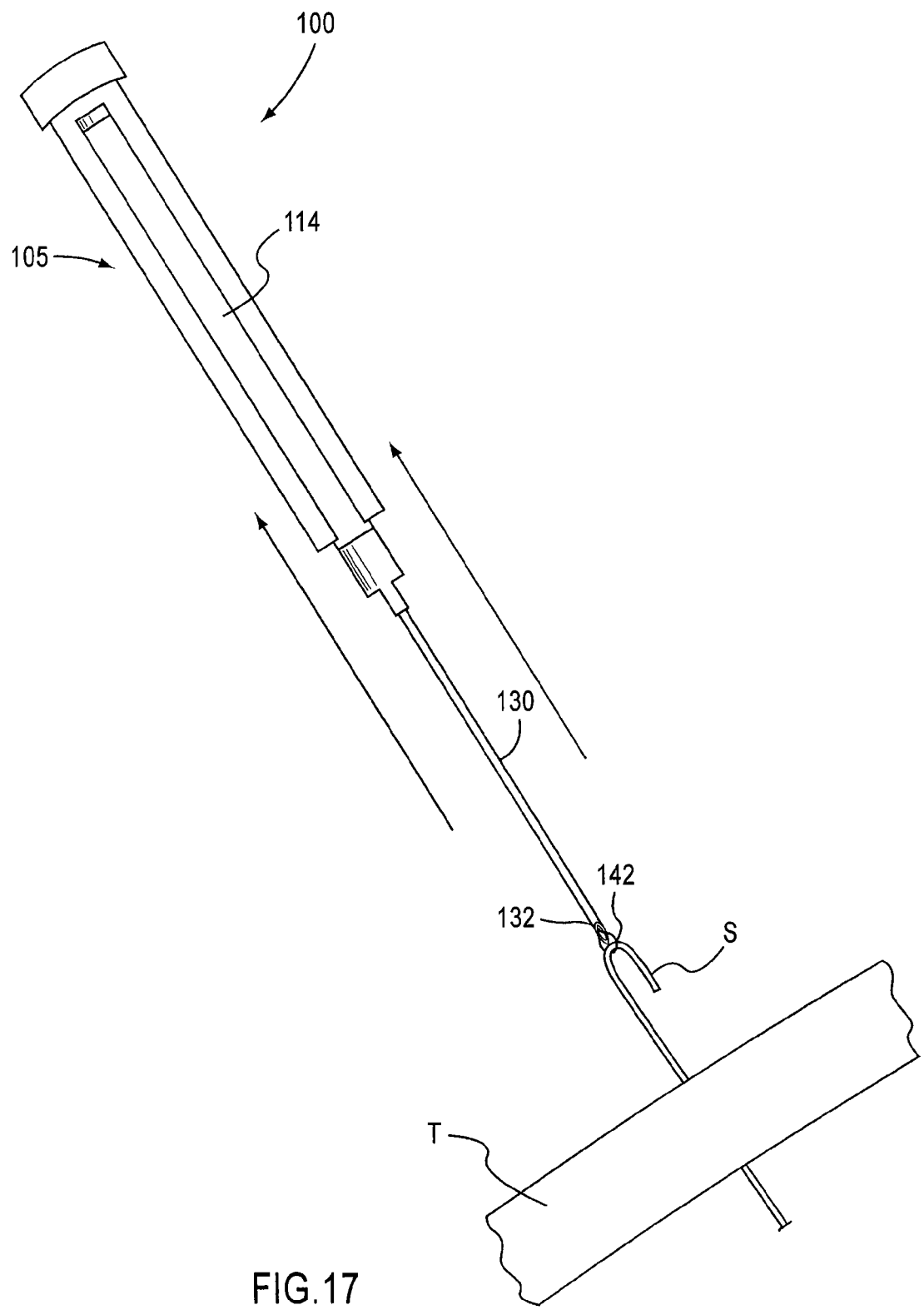
FIG. 17 shows an apparatus according to an embodiment of the invention being withdrawn from bodily tissue and withdrawing a suture through the bodily tissue.

In still another example, although a method of using an apparatus according to an embodiment of the invention is illustrated and described above as including withdrawing the shaft portion 130 from the tissue T as the actuator 114 remains in its second position and the receiving portion 142 remains in its second position, in another embodiment, the actuator, and therefore the receiving portion can be moved to another position before or while being withdrawn from the tissue T. For example, as illustrated in FIGS. 16 and 17, the actuator 114 is moved to move the receiving portion 142 to a position such that the receiving portion is partially retracted into (or disposed within) the lumen 132 of the shaft portion 130.

Thus, the breadth and scope of the invention should not be limited by any of the above-described embodiments, but should be defined only in accordance with the following claims and their equivalents. The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

What is claimed is:

1. An apparatus, comprising:
an elongate member having a handle and a shaft, the shaft having a sharp tip being configured to pierce bodily tissue, the handle being cylindrical, the handle defining a lumen, the handle defining a slot on an outer surface of the handle, the slot extending along an axis parallel to a central axis of the handle, the slot having an open end at a distal end of the handle and a closed end at a proximal end portion of the handle;

an actuator slidably coupled to the handle and being entirely disposed below the outer surface of the handle, the actuator being configured to be accessible through the slot, the actuator being moveable from a first position to a second position different than the first position, the actuator being configured to move along a direction parallel to the central axis from a position in which a portion of the actuator is retracted into the lumen of the handle to a position in which the actuator is at least partially extended from the distal end of the handle; and a thread member having a proximal end portion coupled to the actuator and a distal end portion defining a receiving portion, the thread member being moveable from a first position to a second position different than the first position when the actuator is moved from its first position to its second position, the thread member being entirely disposed within a lumen defined by the shaft when the thread member is in its first position, a portion of the thread member extending from a distal opening defined by the shaft when the thread member is in its second position.

2. The apparatus of claim 1, wherein the receiving portion is disposed within the lumen of the shaft when the actuator is in its first position.

3. The apparatus of claim 1, wherein the actuator is configured to move to a third position different than its first position and its second position, the thread member configured to move to a third position different than its first position and its second position when the actuator is moved to its third position.

4. The apparatus of claim 1, wherein the shaft of the elongate member is configured to penetrate a bodily tissue.

5. The apparatus of claim 1, wherein the shaft is curved at a predetermined angle.

6. The apparatus of claim 1, wherein the shaft is a hypodermic needle.

7. The apparatus of claim 1, wherein the shaft is constructed of a shapeable material.

8. The apparatus of claim 1, wherein the actuator is configured to remain in the first position or the second position by interlocking teeth, the actuator including teeth that lock into grooves formed by complementary teeth inside the handle and beneath the actuator.

9. The apparatus of claim 1, wherein the receiving portion of the thread member is configured to have a preconfigured shape when the receiving portion of the thread member extends from the distal opening of the elongate member.

10. The apparatus of claim 1, wherein the receiving portion of the thread member is formed of a shape memory material.

11. The apparatus of claim 1, wherein, when the thread member is in its second position, the portion of the thread member extending from the distal opening includes the receiving portion and has a shape selected from the group consisting of curved, straight, C-shaped, S-shaped, and U-shaped.

12. The apparatus of claim 1, wherein the receiving portion of the thread member defines an opening configured to receive a thread-like object.

13. An apparatus, comprising:

an elongate member having a handle and a shaft, the shaft having a sharp tip configured to pierce bodily tissue, the handle being cylindrical, the handle defining a lumen, the handle defining an elongate slot on an outer surface of the handle, the elongate slot extending along an axis parallel to a central axis of the handle, the elongate slot having an open end at a distal end of the handle and a closed end at a proximal end portion of the handle, the shaft being a cylindrical tube having a distal end portion suitable for penetrating tissue;

an actuator slidably coupled to the handle and being entirely disposed below the outer surface of the handle, the actuator being accessible through the elongate slot defined by the handle, the actuator being moveable from a first position to a second position different than the first position, the actuator being biased to one of the first position and second position, the actuator being configured to move along a direction parallel to the central axis from a position in which a portion of the actuator is retracted into the lumen of the handle to a position in which the actuator is at least partially extended from the distal end of the handle; and a thread member coupled to the actuator and having a receiving portion, the receiving portion forming a loop defining an opening and being located at the distal-most end of the thread member, the receiving portion being configured to move from a first position to a second position different than the first position when the actuator is moved from its first position to its second position, at least a portion of the loop formed by the receiving portion being disposed within the shaft when the receiving portion is in its first position, at least a portion of the loop formed by the receiving portion extending from a distal opening of the shaft when the receiving portion is in its second position, the receiving portion being configured to have a predetermined shape when the receiving portion is in its second position.

14. A system for passing a suture through bodily tissue, comprising:

an apparatus including an elongate member, an actuator, and a thread member, the elongate member having a handle and a shaft, the shaft having a distal tip and defining a lumen and a distal opening, the shaft having a sharp tip and being configured to be inserted into a first bodily tissue, the handle being cylindrical, the handle defining a lumen, the handle defining a slot on an outer surface of the handle, the slot extending along an axis parallel to a central axis of the handle, the slot having an open end at a distal end of the handle and a closed end at a proximal end portion of the handle;

the actuator coupled to the elongate member and being entirely disposed below the outer surface of the handle, the actuator being moveable from a first position to a second position different than the first position, the actuator being configured to move along a direction parallel to the central axis from a position in which a portion of the actuator is retracted into the lumen of handle to a position in which the actuator is at least partially extended from the distal end of the handle; and the thread member coupled to the actuator and having a receiving portion, the receiving portion forming a loop defining an opening and being located at the distal-most end of the thread member, the thread member being moveable from a first position to a second position different than the first position when the actuator is moved from its first position to its second position, a portion of the loop formed by the receiving portion being disposed within the lumen of the shaft when the thread member is in its first position, the portion of the loop formed by the receiving portion extending from the distal opening of the shaft when the thread member is in its second position; and a backstop, at least a portion of the backstop being configured to be inserted into a body cavity, the backstop having a first portion and a second portion, the second portion extending from the first portion and being disposed at an angle with respect to the first portion, the second portion of the backstop having a covering, the backstop being configured to be disposed within the body cavity such that the second portion is disposed between the first bodily tissue and a second bodily tissue to help prevent the distal tip of the shaft of the elongate member from penetrating the second bodily tissue.

15. The system of claim 14, wherein the second end portion of the backstop being configured to contact the distal tip of the shaft.

16. The system of claim 14, wherein the shaft is configured to be inserted into the first bodily tissue along a first axis, the backstop is configured to be inserted into the body cavity such that a portion of the backstop extends along a second axis, the second axis being angled with respect to the first axis.

17. The system of claim 14, wherein the actuator is biased to one of its first position and its second position.

18. The system of claim 14, wherein the covering includes one of a foam material and gauze.

\* \* \* \* \*